US009470672B2

(12) United States Patent
Liu et al.

(10) Patent No.: US 9,470,672 B2
(45) Date of Patent: Oct. 18, 2016

(54) METHOD FOR TESTING SELF DRYING EFFECT OF CEMENT-BASED MATERIAL

(75) Inventors: Jiaping Liu, Nanjing (CN); Qian Tian, Nanjing (CN); Ting Yao, Nanjing (CN); Yujiang Wang, Nanjing (CN); Yujiang Wang, Nanjing (CN); Hang Zhang, Nanjing (CN); Jianye Zhang, Nanjing (CN)

(73) Assignee: JIANGSU SOBUTE NEW MATERIALS CO., LTD., Nanjing (CN)

( * ) Notice: Subject to any disclaimer, the term of this patent is extended or adjusted under 35 U.S.C. 154(b) by 357 days.

(21) Appl. No.: 14/131,816

(22) PCT Filed: Dec. 30, 2011

(86) PCT No.: PCT/CN2011/085048
§ 371 (c)(1),
(2), (4) Date: Jan. 9, 2014

(87) PCT Pub. No.: WO2013/097189
PCT Pub. Date: Jul. 4, 2013

(65) Prior Publication Data
US 2014/0144217 A1    May 29, 2014

(51) Int. Cl.
*G01N 5/02* (2006.01)
*G01N 33/38* (2006.01)

(52) U.S. Cl.
CPC .................................. *G01N 33/383* (2013.01)

(58) Field of Classification Search
CPC ...... H05B 6/70; H05B 6/80; H05B 2214/02; B64D 43/02; G01P 5/165
USPC ....... 73/73, 76, 170.02; 374/179, 16, 27, 28, 374/142, 208, 163; 136/200
See application file for complete search history.

(56) References Cited

U.S. PATENT DOCUMENTS

| 2,423,447 A * | 7/1947 | Grimm | G01R 19/28 324/119 |
| 4,746,534 A * | 5/1988 | Phillippi | G01K 1/08 374/E1.011 |

(Continued)

FOREIGN PATENT DOCUMENTS

| CN | 101029881 A | 9/2007 |
| CN | 101539566 A | 9/2009 |

(Continued)

OTHER PUBLICATIONS

Grasley et al., Relative Humidity in Concrete, 2016, Concrete International, pp. 51-57.*

(Continued)

*Primary Examiner* — John Fitzgerald
*Assistant Examiner* — Truong Phan
(74) *Attorney, Agent, or Firm* — Treasure IP Group, LLC

(57) ABSTRACT

Disclosed is a method for testing the self-drying effect of a cement-based material, capable of testing the change in humidity of the cement-based material after the final setting until the Id stage of adding water, so as to reflect the water consumption therein and the self-drying course. In the time period after the final setting of the cement-based material until the 1 d stage of adding water and forming, the dew-point temperature inside the cement-based material is tested, and then the relative humidity inside the cement-based material is calculated using a formula. The present invention can test the change in humidity of the cement-based material after the final setting until the Id stage of adding water, so as to reflect the internal water consumption therein and the self-drying course. Further provided is a multi-stage test method for the whole course, capable of testing the whole course of continuous reduction in relative humidity from an initial 100%, in sealed conditions, starting with adding water and formation of the cement-based material, so as to provide a theoretical foundation for the quantitative calculation of the self-drying and shrinking thereof.

3 Claims, 3 Drawing Sheets

(56) References Cited

U.S. PATENT DOCUMENTS

| | | | | |
|---|---|---|---|---|
| 4,822,979 A | * | 4/1989 | deKam | B23K 3/0315 |
| | | | | 219/229 |
| 5,069,726 A | * | 12/1991 | Ragless | H01L 35/34 |
| | | | | 136/200 |
| 5,310,575 A | * | 5/1994 | Friese | G01N 27/4075 |
| | | | | 204/429 |
| 7,234,860 B2 | | 6/2007 | Jensen et al. | |
| 2005/0152431 A1 | * | 7/2005 | Jensen | G01N 25/68 |
| | | | | 374/16 |
| 2007/0246857 A1 | * | 10/2007 | Kurtis | B28B 1/525 |
| | | | | 264/236 |

FOREIGN PATENT DOCUMENTS

| | | | |
|---|---|---|---|
| CN | 101539566 A | * | 9/2009 |
| CN | 102539475 A | | 7/2012 |
| KR | 100515116 | * | 9/2005 |

OTHER PUBLICATIONS

Jiang, Zhengwu, et al, Autogenous relative humidity change and autogenous shrinkage high-performance cenment pastes, cement and concrete research, Aug. 2005, vol. 35, No. 8, pp. 1539-1545.

* cited by examiner

METHOD FOR TESTING SELF DRYING EFFECT OF CEMENT-BASED MATERIAL

CROSS REFERENCE TO RELATED APPLICATION

This application claims priority to, PCT application PCT/CN2011/085048, filed on Dec. 30, 2011, entitled "Method for testing self drying effect of cement based material". The PCT application is incorporated herein by reference in its entirety.

FIELD OF THE INVENTION

The present invention relates to a testing method for self-desiccation effect on cement-based material.

BACKGROUND OF THE INVENTION

Self-desiccation of cement-based material refers to the decreasing of relative humidity caused by internal hydration and chemical shrinkage of the cement-based material under enclosed conditions and exchanges with external substances after it is shaped. Under enclosed conditions, the internal relative humidity of the cement-based material will become unsaturated (<100%) from saturated (100%) because of hydration. It is therefore called self-desiccation. Self-desiccation effect is a drive for autogenous shrinkage of the cement-based material. The self-desiccation degree is the basis to calculate autogenous shrinkage of the cement-based material. Autogenous shrinkage is an important reason cause cement-based material to crack in the early stage.

Conventional method to test self-desiccation effect is to test the internal relative humidity of the cement-based material under enclosed conditions by means of the hygrometer. Along with the development of the modern testing technology, the precision and reliability of the hygrometer are continuously increasing. However, the reliable testing range of the hygrometer is below 99% due to limitation of the testing principle and the equilibration time is fairly long. The relative humidity of the cement in early stages is mostly above 99%. It is a world-wide problem to conduct humidity test under such high humid environment. From the typical humidity curve made via a conventional hygrometer, the real humidity cannot be measured for a long time as the hygrometer is still in the equilibration time after initial setting of the cement. Consequently, we have to wait (it is generally 1 day) until the cement-based material becomes hardened if we intend to use the hygrometer. Additionally, we cannot carry out measurement by using the hygrometer during the period the cement-based material is from being shaped after addition of water to 1 day.

The researcher of this invention has tried to use the principle of tensiometer to test the self-desiccation process (the corresponding relative humidity range is 100%-99.98%) from the cement-based material being shaped after addition of water to the pore's negative pressure becoming about 80 kPa. However, it is found out that 80 kPa is only when the cement-based material is finally set. It is unnecessary to test the water consumption and self-desiccation process (pore's negative pressure is at 80 kPa-2000 kPa and corresponding relative humidity range is at 99.98%-99.5%) when the cement-based material is from final set to water being added for 1 day by using the principle of tensiometer.

SUMMARY OF THE INVENTION

In view of the above-described problems, it is one objective of the present invention to provide a testing method for self-desiccation effect on cement-based material, which is able to test the humidity change of the cement-based material from final set to water being added for 1 day so as to show the water consumption and self-desiccation process inside the cement-based material.

The invention is based on the following principles:

The self-desiccation of the cement-based material caused by hydration and chemical shrinkage is basically a thermodynamic process of the porous material whose internal negative pressure is continuously increasing and whose relative humidity is continuously decreasing. It can be represented by the following two classical equations used in thermodynamics:

Laplace's Equation:

$$\Delta p = \frac{2\gamma \cos\theta}{r} \quad (1)$$

Kelvin's Theorem:

$$RH = \frac{p_g}{p_{sat}} = \exp\left(-\frac{2\gamma M_l \cos\theta}{r\rho_l RT}\right) \quad (2)$$

In the equations (1) and (2), $\gamma$ refers to the gas-liquid interfacial tension, $\theta$ refers to the contact angle, $r$ refers to the critical pore radius, $\Delta P$ refers to the negative pressure of capillary, RH refers to the internal relative humidity of the cement-based material, $p_g$ refers to the saturated vapor pressure of the curved surface water inside pore, $p_{sat}$ refers to the saturated vapor pressure of the plane water, $M_l$ refers to the molar mass of liquid phase, R is an ideal gas constant, T is the absolute temperature and $\rho_l$ is the density of liquid phase.

It is shown from the equations (1) and (2) that the variable to determine the thermodynamic state of the internal moisture of cement-based material is the critical pore radius $r$ when other parameters are given. In accordance with the principle of the lowest energy in thermodynamics, moisture evaporation and consumption always take place from large pores to small pores. Under given thermodynamic state, the pores whose radii are smaller than r are still full of water and whose radii are larger than r not longer have water. The given critical pore radius determines the negative pressure and relative humidity of the pores. In other words, if we can quantitatively measure the negative pressure and relative humidity of the pores of the cement-based material, we can test the internal thermodynamic state change—self-desiccation effect—of the cement-based material caused by hydration and chemical shrinkage under enclosed conditions during the whole process since the cement-based material is shaped after addition of water. Meanwhile, during the continuous increasing of the pore's negative pressure and continuous decreasing of the pore's relative humidity, the critical pore radius gradually becomes smaller, and the corresponding saturated vapor pressure and dew-point temperature gradually falls.

The relationship between the relative humidity and the dew-point temperature can be denoted by the equation (3):

$$\log(RH) = \frac{7.45 \cdot t_d}{235 + t_d} - \frac{7.45 \cdot t}{235 + t} \quad (3)$$

Wherein,

RH refers to the internal relative humidity of the cement-based material;

$t_d$ refers to the dew-point temperature when the pore is of the critical pore radius; and t refers to the ambient temperature.

Consequently, we can calculate the internal relative humidity change by testing the dew-point temperature. In this invention, it is found out from the test that the internal relative humidity change of the cement-based material from final set to water being added for 1 day can be calculated by the above method. In other words, the relative humidity changes between 99.98% and 99.5%. The probe to test the dew-point temperature is the thermocouple probe that is protected either with a porous ceramic cover or a stainless wire mesh. The thermocouple is formed by electrically connected constantan and nichrome. The pore diameter of the porous ceramic cover or the stainless wire mesh is 2-5 μm. The dew-point thermometer is formed by a thermocouple probe and a dew-point microvoltmeter. The dew-point microvoltmeter contains an electronic system and is especially used to test the dew-point temperature via the thermocouple probe. The dew-point thermometer, using the dew-point method, also consists of a sensing circuit and a control circuit, which can automatically maintain the crunodal temperature of the thermocouple.

The testing method for self-desiccation effect on cement-based material uses the dew-point thermometer to test the internal dew-point temperature of the cement-based material from final set to being shaped after addition of water for 1 day and afterwards the relative humidity is calculated according to the equation (3):

$$\log(RH) = \frac{7.45 \cdot t_d}{235 + t_d} - \frac{7.45 \cdot t}{235 + t} \quad (3)$$

Wherein,

RH refers to the internal relative humidity of the cement-based material and RH=99.98%-99.5%;

$t_d$ refers to the dew-point temperature when the pore is of the critical pore radius; and t refers to the ambient temperature;

The dew-point thermometer is formed by a thermocouple probe and a dew-point microvoltmeter, in which the thermocouple probe is protected either with a porous ceramic cover or a stainless wire mesh and the thermocouple is formed by electrically connected constantan and nichrome. The pore diameter of the porous ceramic cover or the stainless wire mesh is 2-5 μm.

As an improvement, during the period the cement-based material is shaped after addition of water to the final set, a negative pressure tester for capillary using the tensiometer principle is used to test the negative pressure of the capillary, and afterwards the internal relative humidity of the cement-based material is calculated according to the equations (1) and (2):

$$\Delta p = \frac{2\gamma \cos\theta}{r} \quad (1)$$

$$RH = \frac{\rho_g}{\rho_{sat}} = \exp\left(-\frac{2\gamma M_l \cos\theta}{r \rho_l RT}\right) \quad (2)$$

In the equations (1) and (2), γ refers to the gas-liquid interfacial tension, θ refers to the contact angle, r refers to the critical pore radius, ΔP refers to the negative pressure of capillary, RH refers to the internal relative humidity of the cement-based material, $p_g$ refers to the saturated vapor pressure of the curved surface water inside pore, $p_{sat}$ refers to the saturated vapor pressure of the plane water, $M_1$ refers to the molar mass of liquid phase, R is an ideal gas constant, T is the absolute temperature and $\rho_1$ is the density of liquid phase.

After the cement-based material is shaped after addition of water for 1 day, the hygrometer can be used to test the initial relative humidity of the hardened cement-based material.

The testing method provided by the invention, no matter the internal relative humidity of the cement-based material is obtained by testing the dew-point temperature or by testing the negative pressure of the capillary, is based on the following premise: carrying out the test under certain ambient temperature and assuming the internal temperature of the cement-based material is the same as the ambient temperature. Under such premise, in the above equations (1) to (3), T=273+t, $M_1$ is 0.018 kg/mol, $\rho_1$ is $1.0 \times 10^3$ kg/m$^3$, saturated vapor pressure $p_{sat}$ of the plane water is the saturated vapor pressure (17.54 mm Hg under 20° C.) under the ambient temperature, and $p_g$ is the saturated vapor pressure inside the pore with critical pore radius r.

The specific operations are as follows (e.g. the relative humidity is fully monitored when the cement-based material is shaped to being added with water for 1 day):

Divide the water-mixed cement-based material into three portions and put them into three completely enclosed containers, which are separately pre-embedded with a negative pressure testing probe for capillary, a dew-point thermometer probe and a hygrometer probe. Please refer to CN200910301734.2 for placement of the negative pressure testing probe for capillary. The dew-point thermometer probe is protected with either stainless steel or ceramic material. It is embedded at least 1 cm depth and the disposable probe directly contacts with the cement-based material so as to ensure the accuracy of the reading. The hygrometer probe can be used with a pre-embedded sleeve to avoid being damaged by the cement-based material and the probe can be repeatedly used. When the pre-embedded sleeve is used, the outer tube is empty and the inner tube is solid and they are both made by stainless steel. The inner tube and the outer tube can be spirally connected together. The inner diameter of the sleeve should be slightly bigger than the outer diameter of the hygrometer probe and the length should be slightly bigger than that of the hygrometer probe, but the difference should not be greater than 5%. The size of the inner tube must be consistent with that of the probe and the wall thickness of the outer tube should not be smaller than 2 mm. During the formation of the cement-based material, the inner tube must be put into the outer tube to be embedded into the cement-based material together. The depth that the tube is embedded is just equal to the length of the sleeve. Remove the inner tube within 2 h after the cement-based material is finally set and put the hygrometer probe with the same size into the outer tube. The end exposed outside can be sealed with cotton.

The upper surfaces of the containers with pre-embedded testing probes also need to be sealed to prevent evaporation of water, and meanwhile they have to be placed in a place with constant temperature of 20° C. and the fluctuation range is no more than ±2° C.

Calculate the relative humidity based on the test data of the negative pressure of the capillary and the equations (1)

and (2) after the cement-based material is shaped after addition of water and before it finally sets.

Afterwards, calculate the relative humidity based on the test data from the dew-point thermometer and the equation (3) after the cement-based material finally set for 1 day.

Use the humidity reading from the hygrometer as the test result from 1 day.

The setting time mentioned in this invention is obtained according to GB 1346—Test Methods for Water Requirement of Normal Consistency, Setting Time and Soundness of the Portland Cement.

The invention can be used to test the humidity change after the cement-based material is from final set to water being added for 1 day so as to show the water consumption and self-desiccation process inside the cement-based material. A testing method with different stages and covering the whole process is further provided to test the whole process of the continuous increasing (from 0 kPa) of the pore's negative pressure and continuous decreasing (from 100%) of the relative humidity caused by hydration and chemical shrinkage when the cement-based material is shaped after addition of water under an enclosed condition. Consequently, it provides a theoretical basis for quantitative calculation of self-desiccation of the cement-based material.

DETAILED DESCRIPTION OF THE EMBODIMENTS

Example 1

Figure 1:
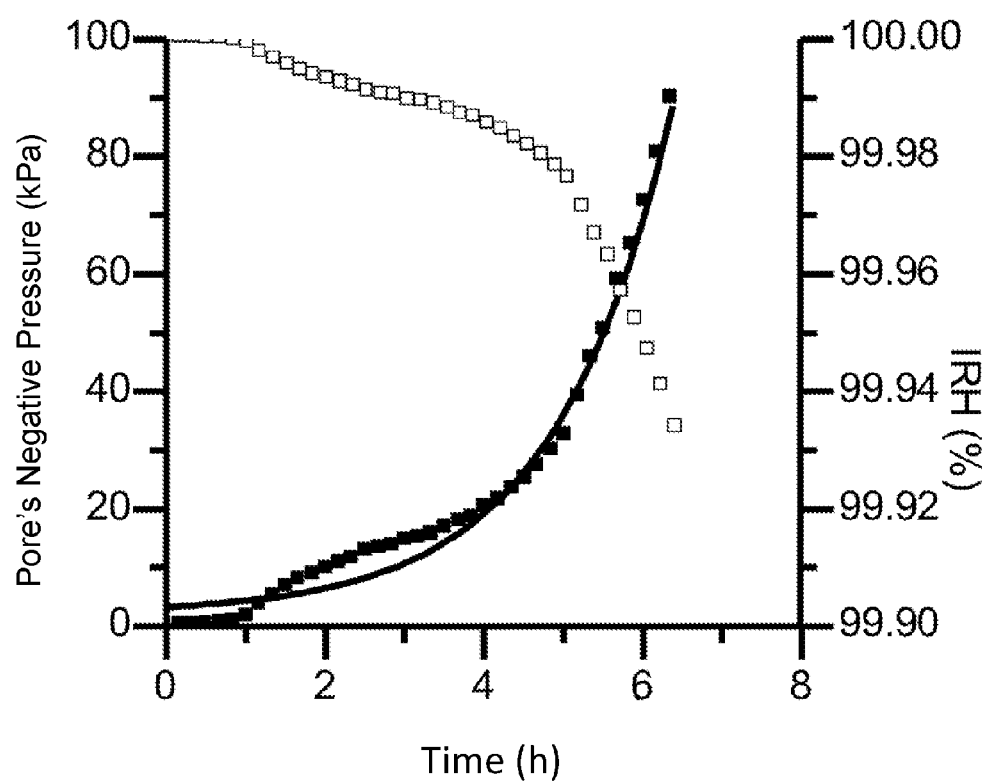
FIG. 1 is a relative humidity change curve of the cement-based material from being shaped after addition of water to final set according to the example 1.
Figure 2:
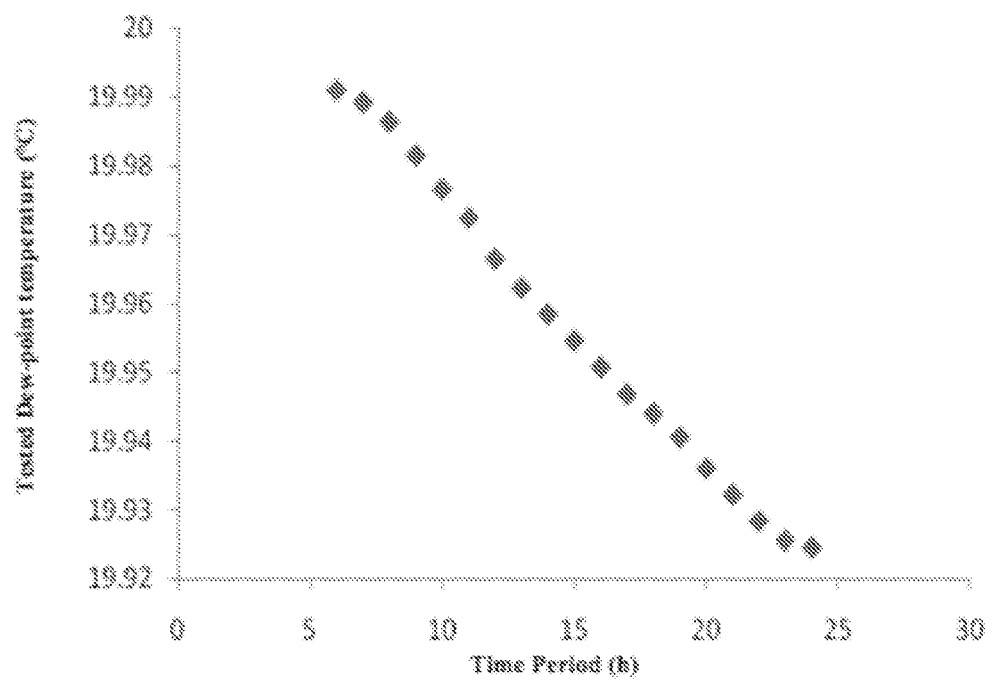
FIG. 2 is a dew-point temperature change curve of the cement-based material from final set to water being added for 1 day according to the example 1.
Figure 3:
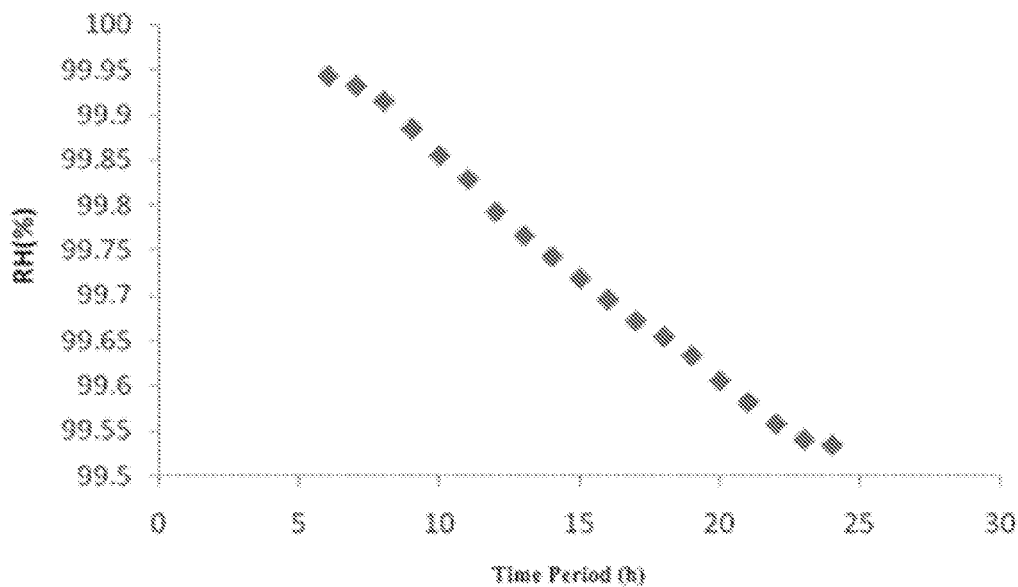
FIG. 3 is a relative humidity change curve of the cement-based material from final set to water being added for 1 day according to the example 1.
Figure 4:
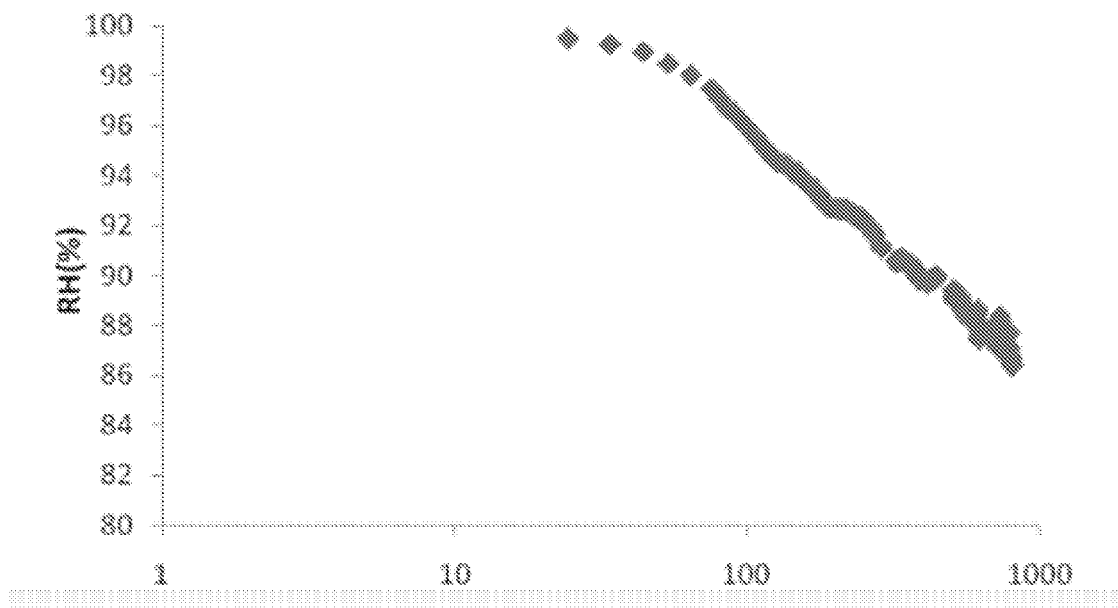
FIG. 4 is a relative humidity change curve of the cement-based material with long time period after water being added for 1 day according to the example 1.

Use Jin Ning Rams Cement 52.5 with water-cement ratio of 0.32 and polycarboxylate superplasticizer of 1.0%. Use a plastic cylinder with diameter of 100 mm and height of 200 mm. The constant water bath temperature is 20° C.±1° C.

Use the negative pressure tester for capillary and its usage mentioned in CN200910301734.2.

The measuring range of the dew-point thermometer is 0-40° C. with precision not less than ±0.005° C. and sensitivity not less than 0.001° C. The probe is the thermocouple probe protected by stainless wire mesh. The thermocouple is formed by electrically connected constantan and nichrome. The pore diameter of the stainless wire mesh is 2 μm. The thermocouple probe is coupled with the dew-point microvoltmeter to form the dew-point thermometer using the dew-point method.

Use HygroClip S humidity sensor made by Rotronic, Switzerland with measuring range of 0-100% RH and precision of ±1.5% RH.

In accordance with GB 1346—Test Methods for Water Requirement of Normal Consistency, Setting Time and Soundness of the Portland Cement, the initial setting time of the cement paste is 4.2 h and the final setting time is 6 h.

There are three stages since the cement-based material is shaped after addition of water according to its hydration and hardening process:

Stage 1: 0 h-6 h. Use the negative pressure tester for capillary to test the initial negative pressure change rules of the capillary and then calculate the decreasing rules of the relative humidity in this stage according to the equations (1) and (2);

Stage 2: 6 h-24 h. Use the dew-point thermometer to test the dew-point temperature change rules and calculate the decreasing rules of the relative humidity in this stage according to the equation (3); and Stage 3: after 24 h. Use the relative hygrometer to directly test the decreasing rules of the relative humidity.

It is found out from the test results that the internal relative humidity of the cement-based material (6 h) calculated via the dew-point thermometer is basically consistent with that calculated via the negative pressure tester for capillary in stage 1. The internal relative humidity of the cement-based material (24 h) calculated via the dew-point thermometer is basically consistent with that calculated via the relative hygrometer in stage 3. Meanwhile, the relative humidity change curve obtained from those three stages conforms to the internal humidity change rules of the cement-based material. The testing method with different stages adopted in this invention solves the problem that the initial self-desiccation effect cannot be measured due to long equilibrium time and initial insensitivity of the hygrometer. It can quantitatively measure the development rules of decreasing of the internal relative humidity, i.e. self-desiccation effect, of the cement-based material caused by hydration during the whole process.

We claim:

1. A three-stage testing method for measuring self-desiccation effect on a cement-based material, comprising:

1) using a negative pressure tester for a capillary according to a tensiometer principle to measure an initial negative pressure of the capillary and then calculating a decreasing rule of an internal relative humidity of the cement-based material in a first stage according to the equations (1) and (2), $$\Delta p = \frac{2\gamma \cos\theta}{r} \quad (1)$$

$$RH = \frac{p_g}{p_{sat}} = \exp\left(-\frac{2\gamma M_l \cos\theta}{r\rho_l RT}\right) \quad (2)$$

in equations (1) and (2), $\gamma$ refers to a gas-liquid interfacial tension, $\theta$ refers to a contact angle, r refers to a critical pore radius, $\Delta P$ refers to a negative pressure of capillary, RH refers to the internal relative humidity of the cement-based material, $p_g$ refers to a saturated vapor pressure of a curved surface water inside a pore, $p_{sat}$ refers to a saturated vapor pressure of a plane water, $M_l$ refers to a molar mass of a liquid phase, R is an ideal gas constant, T is an absolute temperature and $\rho_l$ is a density of the liquid phase;

2) using a dew-point thermometer in a second stage to test an internal dew-point temperature of the cement-based material from final set to being shaped after addition of water for 24 hours, and then calculating an internal relative humidity according to equation (3):

$$\log(RH) = \frac{7.45 \cdot t_d}{235 + t_d} - \frac{7.45 \cdot t}{235 + t} \quad (3)$$

wherein, in equation (3),

RH refers to the internal relative humidity of the cement-based material and RH=99.98%-99.5%;

$t_d$ refers to a dew-point temperature when the pore is of a critical pore radius; and t refers to an ambient temperature;

wherein, the dew-point thermometer is formed by a thermocouple probe and a dew-point microvoltmeter, in which the thermocouple probe is protected either with a porous ceramic cover or a stainless wire mesh and the thermocouple is formed by electrically connected constantan and nichrome; the pore diameter of the porous ceramic cover or diameter of the stainless wire mesh is 2-5 μm;

3) using a relative hygrometer to monitor a decrease in the internal relative humidity of the cement-based material in a third stage;

wherein, the first stage occurs from the cement-based material being shaped after addition of water to final set, which is 0-6 hours since the cement-based material is shaped after addition of water;

the second stage occurs from final set to 24 hours after water being added, which is 6-24 hours since the cement-based material is shaped after addition of water; and the third stage occurs after 24 hours after watering being added, which is after 24 hours since the cement-based material is shaped after addition of water.

2. The testing method for self-desiccation effect on cement-based material of claim 1, wherein a measuring range of the dew-point thermometer is 0–40° C., a precision is not less than ±0.005° C. and the sensitivity is at least 0.001° C.

3. The testing method for self-desiccation effect on cement-based material of claim 1, wherein when the dew-point thermometer is used to calculate the internal dew-point temperature of the cement-based material, the thermocouple probe is embedded at least 1 cm depth.

* * * * *